(12) United States Patent
Hazebrouck et al.

(10) Patent No.: US 8,470,047 B2
(45) Date of Patent: Jun. 25, 2013

(54) FIXED-BEARING KNEE PROSTHESIS

(75) Inventors: Stephen A. Hazebrouck, Winona Lake, IN (US); Daren L. Deffenbaugh, Winona Lake, IN (US); Paul S. Randall, South Weymouth, MA (US)

(73) Assignee: DePuy (Ireland) (IE)

( * ) Notice: Subject to any disclaimer, the term of this patent is extended or adjusted under 35 U.S.C. 154(b) by 1330 days.

(21) Appl. No.: 11/860,833

(22) Filed: Sep. 25, 2007

(65) Prior Publication Data

US 2009/0082873 A1   Mar. 26, 2009

(51) Int. Cl.
*A61F 2/38* (2006.01)
(52) U.S. Cl.
USPC ................................ 623/20.32; 623/20.31
(58) Field of Classification Search
USPC ................. 623/20.31, 20.32, 20.29, 20.28
See application file for complete search history.

(56) References Cited

U.S. PATENT DOCUMENTS

| 4,257,129 A | 3/1981 | Volz |
| 4,673,407 A | 6/1987 | Martin |
| 4,714,474 A | 12/1987 | Brooks, Jr. et al. |
| 4,795,468 A | 1/1989 | Hodorek et al. |
| 4,822,362 A | 4/1989 | Walker et al. |
| 4,944,757 A | 7/1990 | Martinez et al. |
| 5,271,737 A | 12/1993 | Baldwin et al. |
| 5,344,460 A | 9/1994 | Turanyi et al. |
| 5,370,699 A | 12/1994 | Hood et al. |
| 5,405,396 A | 4/1995 | Heldreth et al. |
| 5,413,604 A | 5/1995 | Hodge |
| 5,480,446 A | 1/1996 | Goodfellow et al. |
| 5,824,103 A | 10/1998 | Williams |
| 5,871,545 A | 2/1999 | Goodfellow et al. |
| 5,879,394 A | 3/1999 | Ashby et al. |
| 5,957,979 A | 9/1999 | Beckman et al. |
| 5,964,808 A | 10/1999 | Blaha et al. |
| 6,039,764 A | 3/2000 | Pottenger et al. |

(Continued)

FOREIGN PATENT DOCUMENTS

| EP | 0 495 340 | 12/1991 |
| FR | 2 653 992 | 10/1991 |
| GB | 2293109 | 3/1996 |
| WO | WO 99/66864 | 12/1999 |

OTHER PUBLICATIONS

Johnson & Johnson Orthopaedics, "Primary Cruciate-Retaining & Cruciate-Substituting Procedure", Reference Guide for Use with P.F.C. Sigma Knee Systems, 1998.

(Continued)

*Primary Examiner* — Bruce E Snow
*Assistant Examiner* — Melissa Hoban
(74) *Attorney, Agent, or Firm* — Barnes & Thornburg LLP

(57) ABSTRACT

A fixed-bearing prosthesis includes a femoral component having a medial condyle surface and a lateral condyle surface. The knee prosthesis also includes a bearing having a medial bearing surface configured to articulate with the medial condyle surface of the femoral component, and a lateral bearing surface configured to articulate with the lateral condyle surface of the femoral component. A tibial tray is secured to the bearing. The tibial tray has a platform with an elongated stem extending downwardly from a lower surface thereof. A peripheral rail extends along at least an anterior section of the perimeter of the tray's platform. The peripheral rail extends upwardly from an upper surface of the platform. A retaining rail extends upwardly from the upper surface of the platform and posteriorly away from the peripheral rail.

18 Claims, 11 Drawing Sheets

U.S. PATENT DOCUMENTS

| | | |
|---|---|---|
| 6,068,658 A | 5/2000 | Insall et al. |
| 6,090,144 A | 7/2000 | Letot et al. |
| 6,162,254 A | 12/2000 | Timoteo |
| 6,280,476 B1 | 8/2001 | Stanley et al. |
| 6,299,646 B1 | 10/2001 | Chambat et al. |
| 6,379,388 B1 | 4/2002 | Ensign et al. |
| 6,869,448 B2 | 3/2005 | Tuke et al. |
| 6,986,791 B1 * | 1/2006 | Metzger ............... 623/20.24 |
| 2003/0139817 A1 * | 7/2003 | Tuke et al. ............ 623/20.32 |
| 2004/0186583 A1 * | 9/2004 | Keller ................... 623/20.24 |
| 2004/0215345 A1 | 10/2004 | Perrone, Jr. et al. |
| 2005/0021147 A1 | 1/2005 | Tarabichi |
| 2005/0055102 A1 * | 3/2005 | Tornier et al. ......... 623/20.32 |
| 2005/0203631 A1 * | 9/2005 | Daniels et al. ......... 623/20.32 |
| 2005/0209702 A1 | 9/2005 | Todd et al. |
| 2006/0036329 A1 * | 2/2006 | Webster et al. ........ 623/20.33 |

OTHER PUBLICATIONS

European Search Report for European Patent Application No. 08164944.4-2310 / 2042131, Mar. 16, 2009, 12 pgs.

* cited by examiner

FIXED-BEARING KNEE PROSTHESIS

TECHNICAL FIELD

The present disclosure relates generally to an implantable orthopaedic prosthesis, and more particularly to an implantable knee prosthesis.

BACKGROUND

During the lifetime of a patient, it may be necessary to perform a joint replacement procedure on the patient as a result of, for example, disease or trauma. The joint replacement procedure may involve the use of a prosthesis which is implanted into one or more of the patient's bones. In the case of a knee replacement procedure, a tibial tray is implanted into the patient's tibia. A bearing is then secured to the tibial tray. The condyle surfaces of the patient's femur, or the condyle surfaces of a replacement femoral component, bear against the tibial bearing.

One type of knee prosthesis is a fixed-bearing knee prosthesis. As its name suggests, the bearing of a fixed-bearing knee prosthesis does not move relative to the tibial tray. Fixed-bearing designs are commonly used when the condition of the patient's soft tissue (i.e., knee ligaments) does not allow for the use of a knee prosthesis having a mobile bearing.

SUMMARY

According to one aspect, a fixed-bearing knee prosthesis includes a femoral component having a medial condyle surface and a lateral condyle surface. The knee prosthesis also includes a bearing having a medial bearing surface configured to articulate with the medial condyle surface of the femoral component, and a lateral bearing surface configured to articulate with the lateral condyle surface of the femoral component. A tibial tray is secured to the bearing. The tibial tray has a platform with an elongated stem extending downwardly from a lower surface thereof. A peripheral rail extends along at least an anterior section of the perimeter of the tray's platform. The peripheral rail extends upwardly from an upper surface of the platform. A retaining rail extends posteriorly away from the peripheral rail.

In some embodiments, the retaining rail has posterior width defined by the distance between a lateral end and a posterior end of a posterior-most edge of the retaining rail and a length defined by the distance of an imaginary center line segment extending from the anterior edge of the tibial tray to a midpoint located along the posterior-most edge halfway between the lateral end and the medial end. The posterior width of the retaining rail is less than, or equal to, the length of the retaining rail.

In certain embodiments, the peripheral rail extends along the entire perimeter of the platform. Moreover, the retaining rail may be contiguous with the peripheral rail.

The peripheral rail may have at least one undercut slot formed therein, with the bearing having at least one tab positioned in the at least one undercut slot of the peripheral rail.

The lower surface of the platform may have a recess formed therein, with the retaining rail being positioned in the recess. Illustratively, the recess is bounded by a sidewall which contacts the retaining rail.

According to another aspect, an implantable orthopaedic component includes a tibial tray configured to be secured to a surgically prepared tibia of a patient. The tibial tray has a platform with an elongated stem extending downwardly from a lower surface thereof. A peripheral rail extends along at least an anterior section of the perimeter of the tray's platform. The peripheral rail extends upwardly from an upper surface of the platform. A retaining rail extends posteriorly away from the peripheral rail.

In some embodiments, the retaining rail has posterior width defined by the distance between a lateral end and a posterior end of a posterior-most edge of the retaining rail and a length defined by the distance of an imaginary center line segment extending from the anterior edge of the tibial tray to a midpoint located along the posterior-most edge halfway between the lateral end and the medial end. The posterior width of the retaining rail is less than, or equal to, the length of the retaining rail.

In certain embodiments, the peripheral rail extends along the entire perimeter of the platform. Moreover, the retaining rail may be contiguous with the peripheral rail.

The peripheral rail may have at least one undercut slot formed therein, with the bearing having at least one tab positioned in the at least one undercut slot of the peripheral rail.

The lower surface of the platform may have a recess formed therein, with the retaining rail being positioned in the recess. Illustratively, the recess is bounded by a sidewall which contacts the retaining rail.

According to one aspect, a fixed-bearing knee prosthesis includes a femoral component having a medial condyle surface and a lateral condyle surface. The knee prosthesis also includes a bearing having a medial bearing surface configured to articulate with the medial condyle surface of the femoral component, and a lateral bearing surface configured to articulate with the lateral condyle surface of the femoral component. A tibial tray is secured to the bearing. The tibial tray has a platform with an elongated stem extending downwardly from a lower surface thereof. A peripheral rail extends along at least an anterior section of the perimeter of the tray's platform. The peripheral rail extends upwardly from an upper surface of the platform. A retaining rail extends posteriorly away from the peripheral rail.

In some embodiments, the peripheral rail has a posterior-most edge that includes a lateral end and a medial end, a lateral-most edge extending linearly from a first point on the peripheral rail to the lateral end of the posterior-most edge, and a medial-most edge extending linearly from a second point on the peripheral rail to the medial end of the posterior-most edge.

In certain embodiments, the peripheral rail extends along the entire perimeter of the platform. Moreover, the retaining rail may be contiguous with the peripheral rail.

The peripheral rail may have at least one undercut slot formed therein, with the bearing having at least one tab positioned in the at least one undercut slot of the peripheral rail.

The lower surface of the platform may have a recess formed therein, with the retaining rail being positioned in the recess. Illustratively, the recess is bounded by a sidewall which contacts the retaining rail.

BRIEF DESCRIPTION OF THE DRAWINGS

The detailed description particularly refers to the following figures, in which.

DETAILED DESCRIPTION OF THE DRAWINGS

Figure 1:
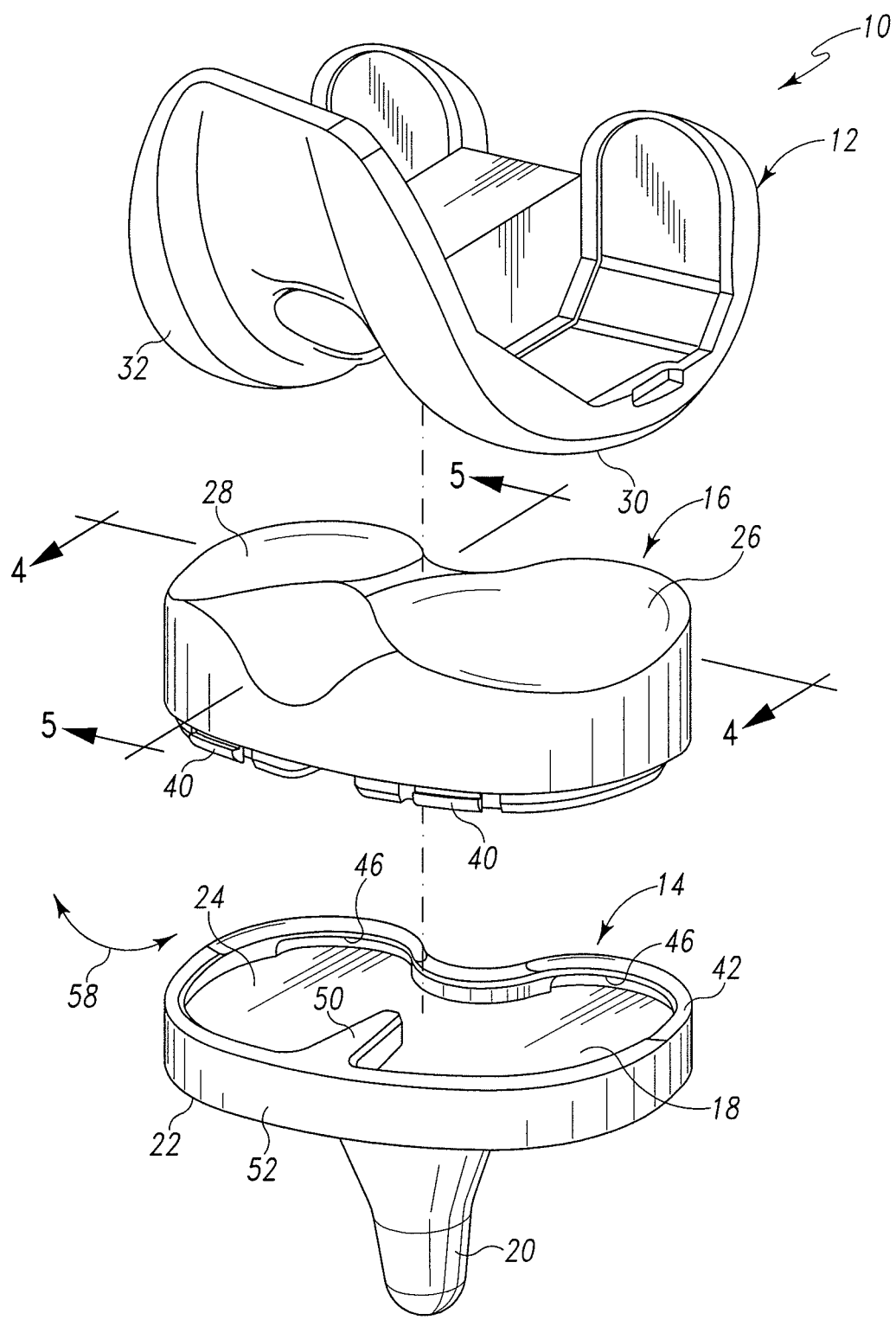
FIG. 1 is an exploded perspective view of a fixed-bearing knee prosthesis.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Referring now to FIGS. 1-6, there is shown a fixed-bearing knee prosthesis 10. The knee prosthesis 10 includes a femoral component 12, a tibial tray 14, and a bearing 16. The tibial tray 14 includes a platform 18 having a stem 20 extending away from its lower surface 22. The tibial stem 20 is configured to be implanted into a surgically prepared end of a patient's tibia (not shown). The bearing 16 is securable to the tibial tray 14. In particular, as will be discussed below in greater detail, the bearing 16 may be snap-fit to the tibial tray 14. In such a way, the bearing 16 is fixed relative to the tibial tray 14 (i.e., it is not rotatable or moveable in the anterior/posterior or medial/lateral directions).

The bearing 16 includes a lateral bearing surface 26 and a medial bearing surface 28. The bearing surfaces 26, 28 are configured to articulate with a lateral condyle surface 30 and a medial condyle surface 32, respectively, of the femoral component 12. Specifically, the femoral component 12 is configured to be implanted into a surgically prepared end of the patient's femur (not shown), and is configured to emulate the configuration of the patient's natural femoral condyles. As such, the lateral condyle surface 30 and the medial condyle surface 32 are configured (e.g., curved) in a manner which mimics the condyles of the natural femur. The lateral condyle surface 30 and the medial condyle surface 32 are spaced apart from one another thereby defining an intercondylar notch therebetween.

The components of the knee prosthesis 10 that engage the natural bone, such as the femoral component 12 and the tibial tray 14, may be constructed with a biocompatible metal, such as a cobalt chrome alloy, although other materials may also be used. The bone engaging surfaces of these components may be textured to facilitate cementing the component to the bone. Such surfaces may also be porous coated to promote bone ingrowth for permanent fixation.

The bearing 16 may be constructed with a material that allows for smooth articulation between the bearing 16 and the femoral component 12, such as a polymeric material. One such polymeric material is polyethylene such as ultrahigh molecular weight polyethylene (UHMWPE).

Figure 2:
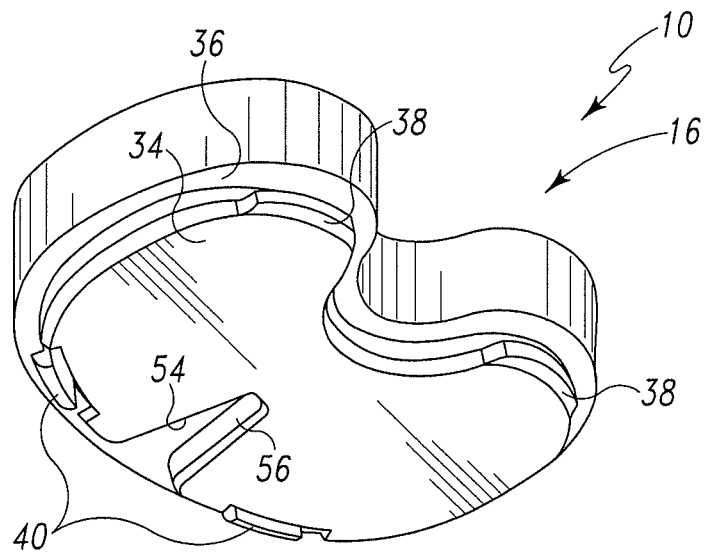
FIG. 2 is a bottom perspective view of the bearing of the knee prosthesis of FIG. 1.
Figure 3:
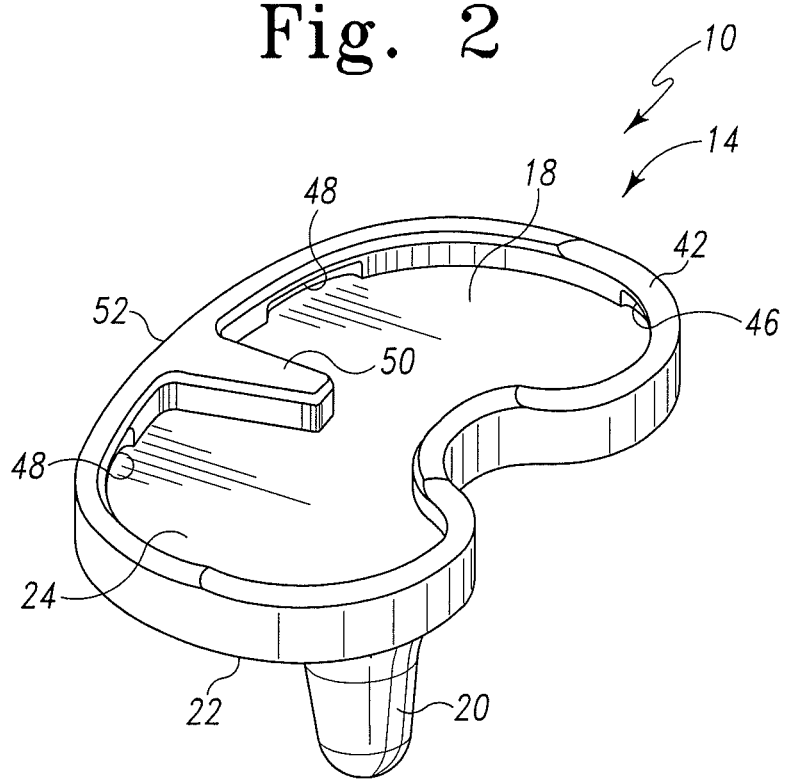
FIG. 3 is a perspective view of the tibial tray of the knee prosthesis of FIG. 1.
Figure 4:
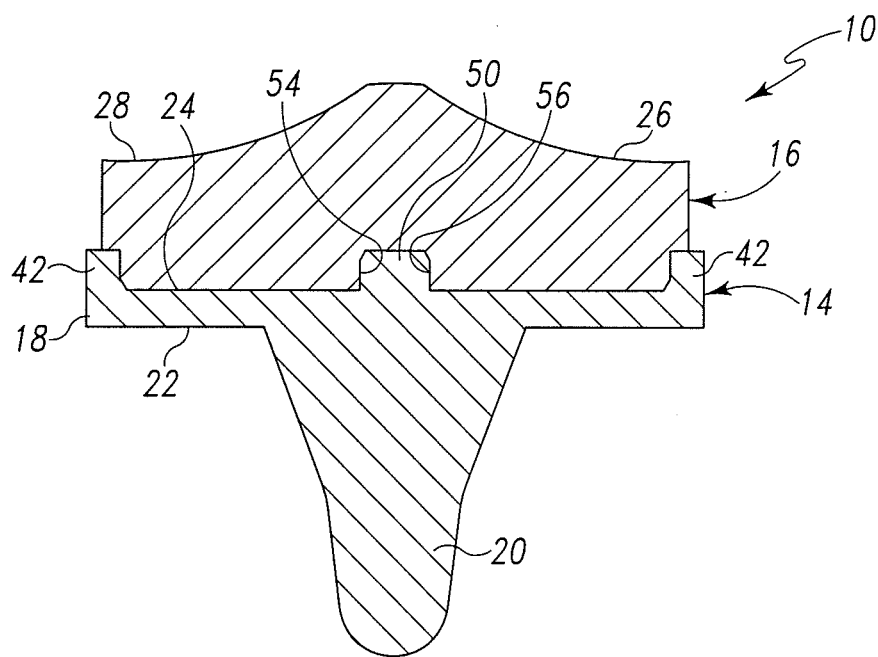
FIG. 4 is a cross sectional view of the assembled knee prosthesis of FIG. 1 taken along the line 4-4 of FIG. 1, as viewed in the direction of the arrows.
Figure 5:
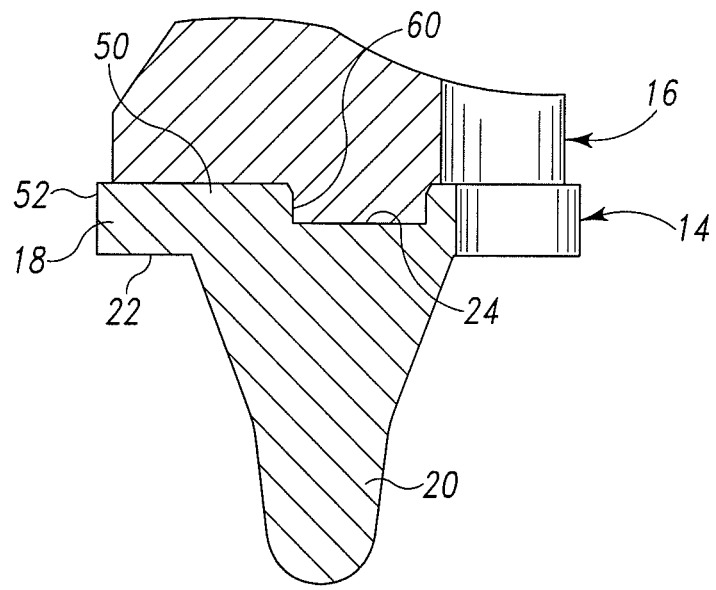
FIG. 5 is a cross sectional view of the assembled knee prosthesis of FIG. 1 taken along the line 5-5 of FIG. 1, as viewed in the direction of the arrows.

As shown in FIGS. 2 and 3, the lower surface 36 of the bearing 16 includes a pedestal 34. The pedestal 34 has a number of posterior tabs 38 defined therein. A number of anterior tabs 40 are also defined in the bearing 16.

As shown in FIG. 3, the knee prosthesis 10 has a peripheral locking mechanism. In particular, a peripheral rail 42 extends upwardly from the upper surface 24 of the tibial tray 14. In the illustrative embodiment described herein, the peripheral rail 42 extends around the entire periphery of the tibial tray 14. However, it is contemplated that the peripheral rail may extend around only certain portions of the parameter of the tibial tray 14, such as a section of the perimeter located on the anterior side of the tibial tray 14. The peripheral rail 42 has a number of posterior undercuts 46 defined therein. Moreover, a number of anterior undercuts 48 are defined in the anterior portions of the peripheral rail 42.

To secure the tibial bearing 16 to the tibial tray 14, the posterior tabs 38 of the bearing 16 are positioned in the posterior undercuts 46 of the tibial tray 14. Thereafter, the anterior portion of the tibial bearing 16 is then advanced downwardly toward the tibial tray 14 such that the pedestal 34 of the bearing's lower surface 36 is captured within the peripheral rail 42. As the anterior portion of the bearing 16 is advanced in such a manner, the anterior tabs 40 of the tibial bearing 16 are deflected by the peripheral rail 42 and thereafter snapped into the anterior undercuts 48 of the peripheral rail thereby securing the bearing 16 to the tray 14.

The upper surface 24 of the tray's platform 18 has a retaining rail 50 extending upwardly therefrom. In the illustrative embodiment described herein, the retaining rail 50 is embodied as an elongated tongue or flange which extends posteriorly from the anterior edge 52 of the tibial tray 14. In the illustrative embodiment described herein, the retaining rail 50 is contiguous with the peripheral rail 42, although the two rails 50, 42 could be embodied separately. Moreover, the retaining rail 50 is herein described as being of a similar height to the peripheral rail, although the components could be embodied has having dissimilar heights.

The lower surface 36 of the bearing 16 has a complimentary-shaped recess 54 defined therein. The recess 54 is bounded by a sidewall 56. As shown in the cross-sectional views of FIGS. 4 and 5, when the bearing 16 is secured to the tibial tray 14, the sidewall 56 of the recess 54 contacts the edges of the retaining rail 50. The dimensions of the recess 54 and the retaining rail 50 are selected such that a relatively tight fit is achieved. In such a way, the bearing 16 is fixed relative to the tibial tray 14. In particular, the configuration of the retaining rail 42 and the pedestal 34 formed in the lower surface 36 of the bearing 16 prevent movement of the bearing 16 relative the tibial tray 14 in the anterior/posterior direction and the medial/lateral direction. Moreover, the tabs 38, 40 positioned in the undercuts 46, 48 prevent lift off of the bearing 16 from the tibial tray 14. Rotational micromotion in the direction of arrow 58 of FIG. 1 is reduced, if not prevented all together, by the relatively tight fit of the retaining rail 50 of the tibial tray 14 into the recess 54 of the bearing.

Figure 6:
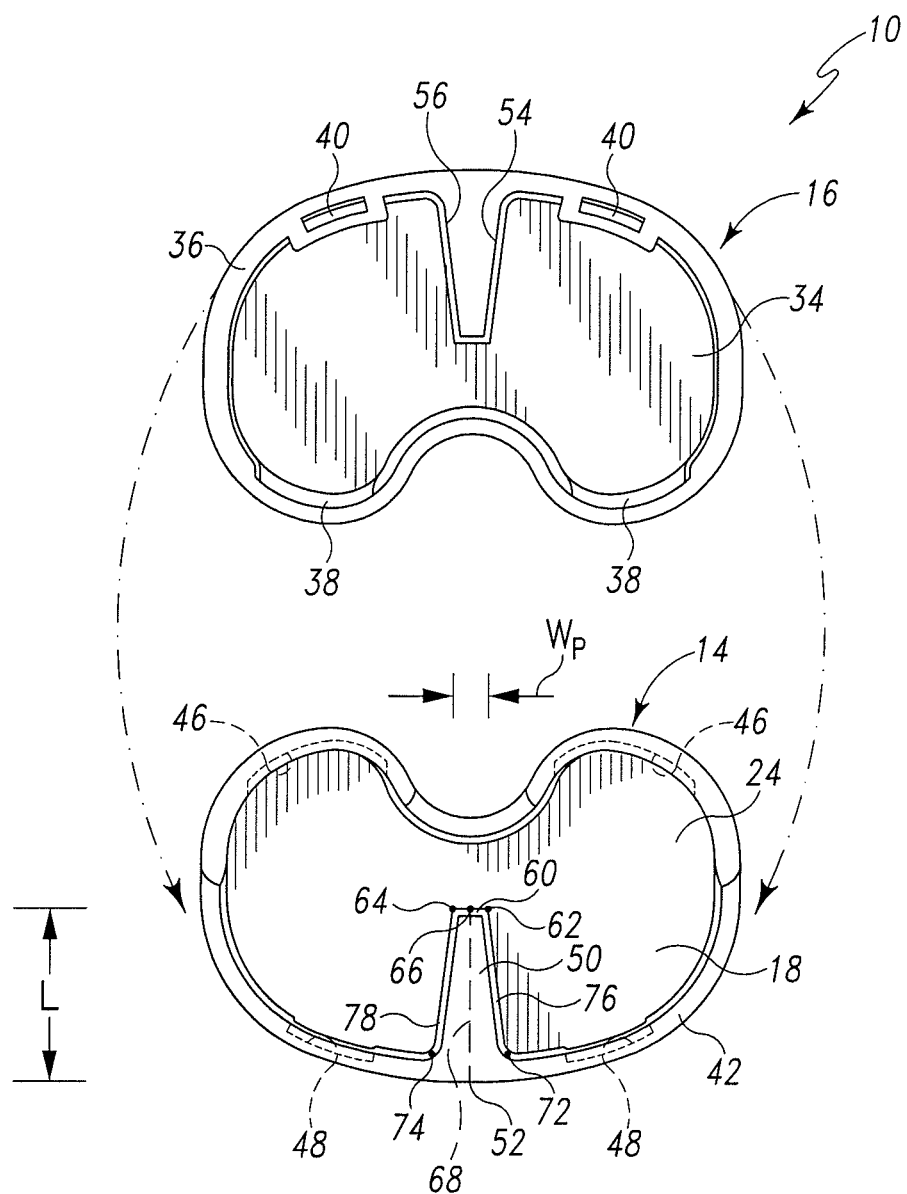
FIG. 6 is an exploded view of the knee prosthesis of FIG. 1, note the tibial tray is shown in a plan view and the bearing is shown in bottom elevational view.

As alluded to above, in the illustrative embodiment described herein, the retaining rail 50 is embodied as an elongated tongue or flange which extends posteriorly from the anterior edge 52 of the tibial tray 14 in a direction toward the center of the tray's platform 18. As shown in FIG. 6, the retaining rail 50 includes a posterior-most edge 60 having a lateral end 62 and a medial end 64. A posterior width (Wp) of the retaining rail 50 is defined by the distance between the lateral end 62 and the medial end 64 of the rail's posterior-most edge 60. The length (L) of the retaining rail 50 is defined by the distance between its posterior most edge 60 and the anterior edge 52 of the tibial tray 14. Specifically, as shown in FIG. 6, a midpoint 66 is located halfway between the lateral end 62 of the posterior-most edge 60 and the medial end 64 of the posterior-most edge 62. An imaginary center line segment 68 extends from the anterior edge 52 of the tibial tray 14 to the midpoint 66. As shown in FIG. 6, the imaginary center line segment 68 bisects the retaining rail 50. Because the retaining rail 50 is embodied as an elongated tongue or flange, the posterior width (Wp) of the retaining rail 50 (i.e., the distance between the ends 62, 64 of the posterior most edge 60) is less than, or equal to, the length (L) of the retaining rail 50. As shown in FIGS. 7-13, such is the case throughout numerous illustrative embodiments of the retaining rail 50.

As also shown in FIG. 6, the retaining rail 50 of the tibial tray 14 has a lateral-most edge 76 which extends linearly from a point 72 on the peripheral rail 42 located on the anterior side of the tray 14 to the lateral end 62 of the posterior-most edge 60 (i.e., extends along a straight line from the point 72 on the peripheral rail 42 to the lateral end 62 of the posterior most edge 60). The retaining rail 50 also includes a medial-most edge 78 that extends linearly from another point 74 on the peripheral rail 42 located on the anterior side of the tray 14 to the medial end 64 o the posterior-most edge 60 (i.e., extends along a straight line from the point 74 on the peripheral rail 42 to the medial end 64 of the posterior most edge 60).

Figure 7:
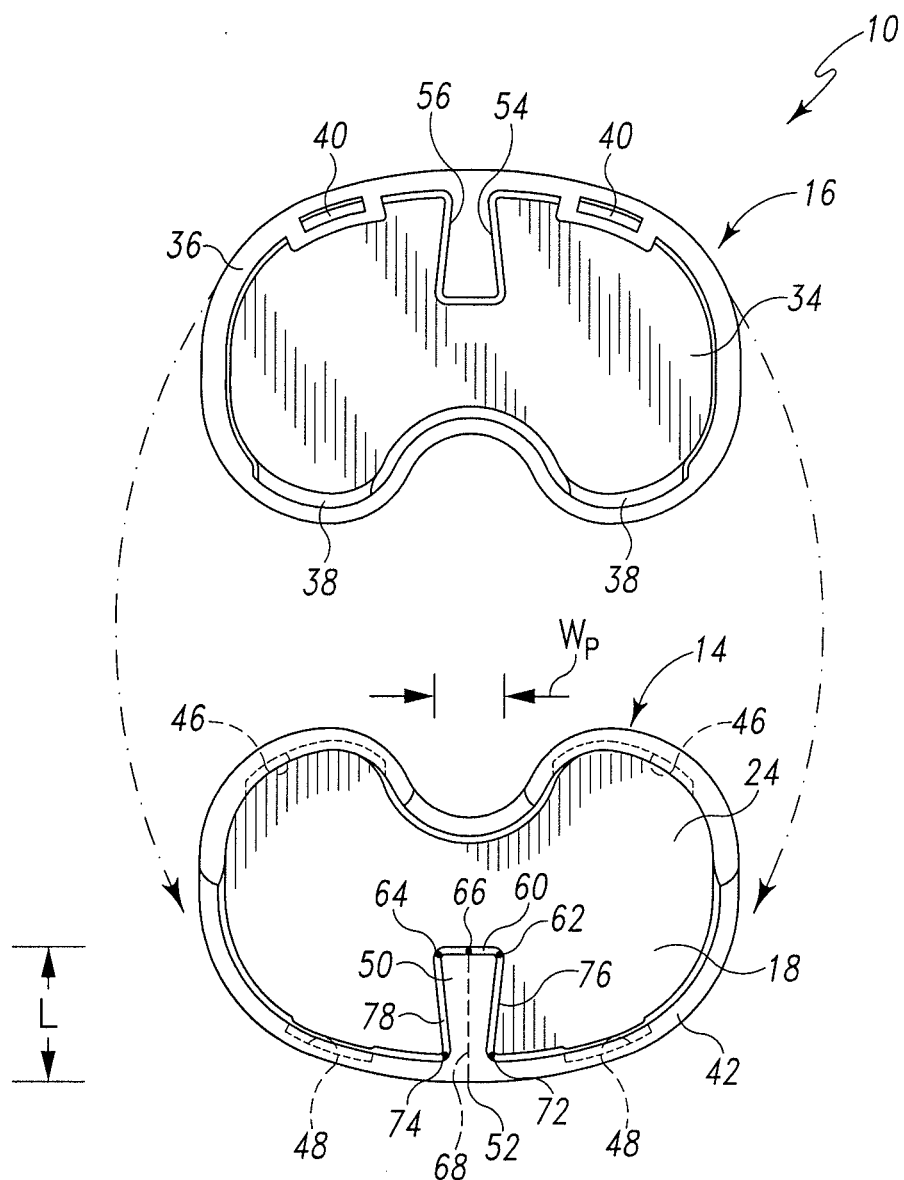
FIGS. 7-13 are similar to FIG. 6, but showing different embodiments of the tibial tray and the bearing.

As shown in FIG. 6, in the illustrative embodiment described herein, the retaining rail 50 is tapered along its length. In particular, the width of the retaining rail 50 is smallest at its posterior-most edge 60, but gradually increases in the direction toward the anterior edge 52 of the tibial tray 14. It should be appreciated, however, that numerous other designs of the retaining rail 50 are contemplated. For example, as shown in FIG. 7, a somewhat inverted design may be used. In the case of FIG. 7, the posterior-most edge 60 of the retaining rail 50 is wider than the edge of the retaining rail 50 along the anterior edge 52 of the tibial tray 14. In other words, the retaining rail 50 shown in FIG. 7 is tapered in the opposite direction to that of the retaining rail 50 shown in FIG. 6. It should be appreciated that the recess 54 defined in the lower surface 36 of the bearing 16 is likewise reshaped in the embodiment of FIG. 7 to accommodate the different shape of the retaining rail 50. In other words, while its contemplated that the design of the retaining rail 50 may be altered, it is also contemplated that the design of the recess 54 is altered accordingly to compliment the configuration of the retaining rail 50.

Figure 8:
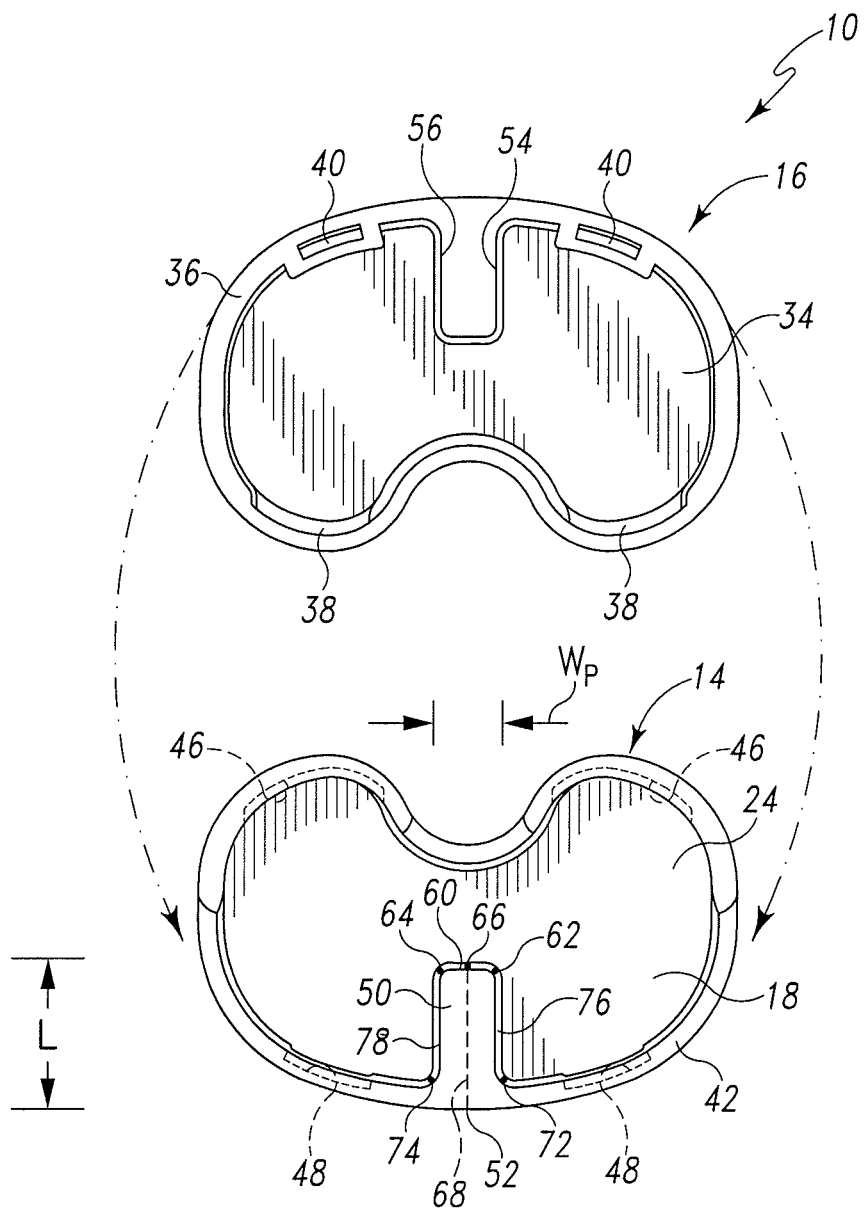
Figure 9:
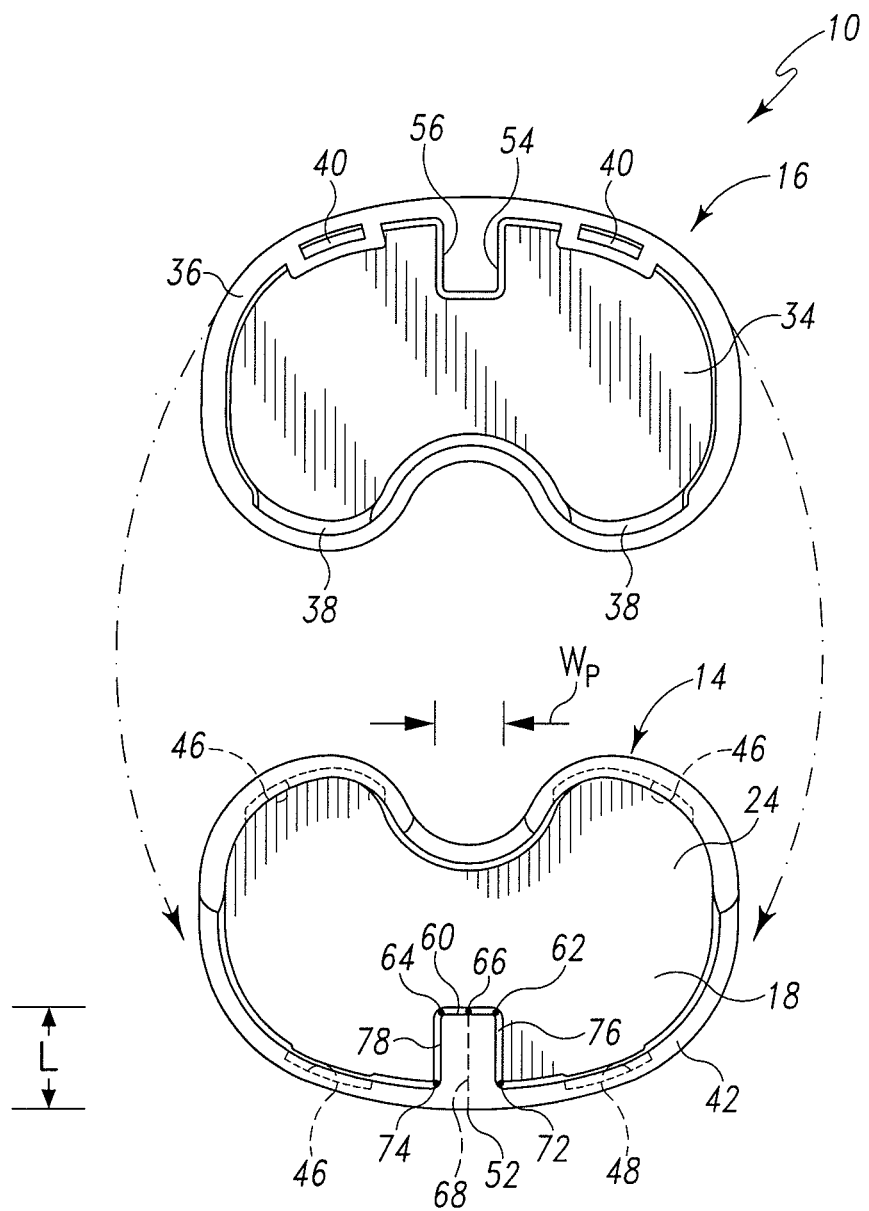
Figure 10:
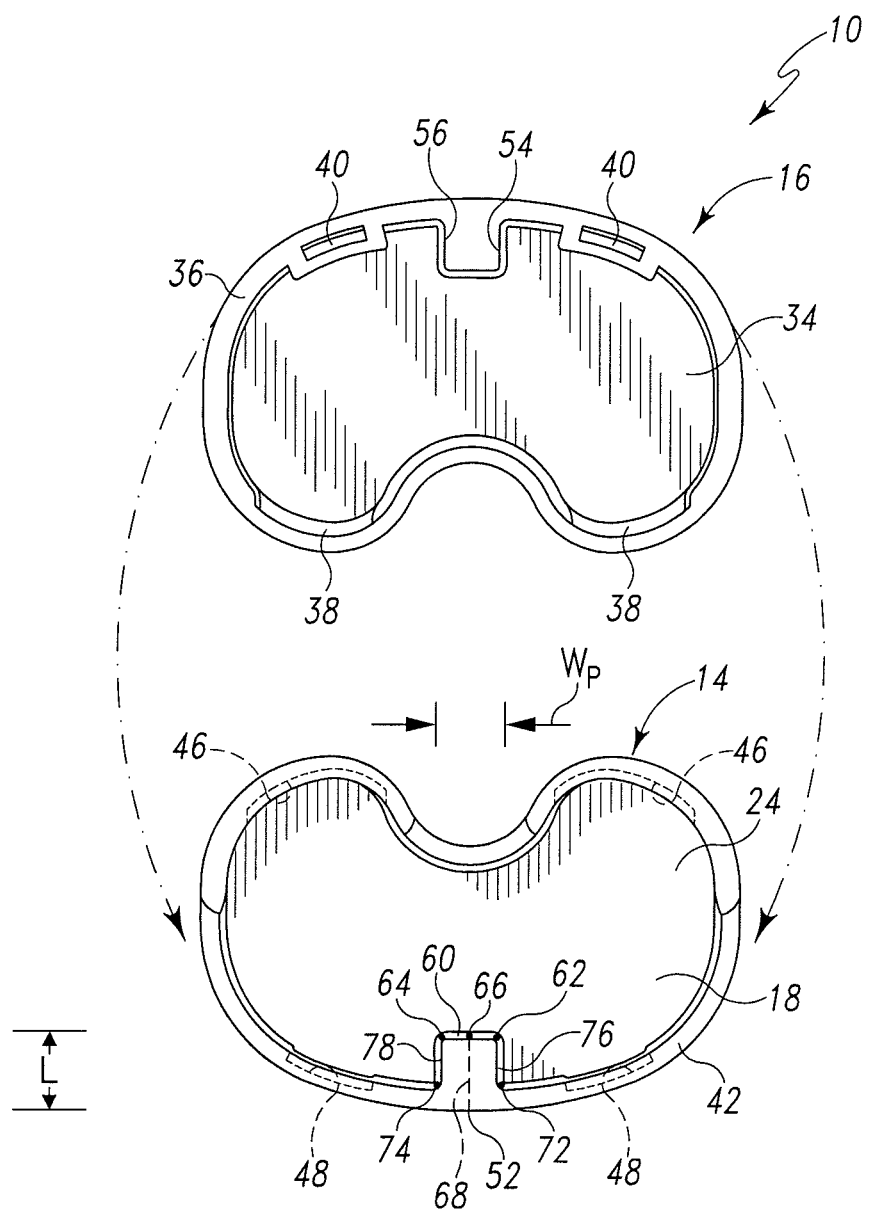

As shown in FIGS. 8-10, non-tapered configurations of the retaining rail 50 may also be used. In such cases, the retaining rail 50 has a substantially constant width throughout its entire length. As demonstrated in the embodiments of FIGS. 8-10, the length (L) of such a non-tapered rail may likewise be varied. However, in each case, the posterior width (Wp) of the retaining rail 50 is less than, or equal to, the length (L) of the retaining rail 50. It should be appreciated that the length (L) of any of the retaining rails described herein, including the tapered retaining rails of FIGS. 6 and 7, may also be varied to fit the needs of a given implant design.

In each of the embodiments shown in FIGS. 8-10, the configuration and dimensions of the corresponding recess 54 defined in the lower surface 36 of the bearing 16 is coordinated to achieve the desired tight fit with its corresponding retaining rail 50.

Figure 11:
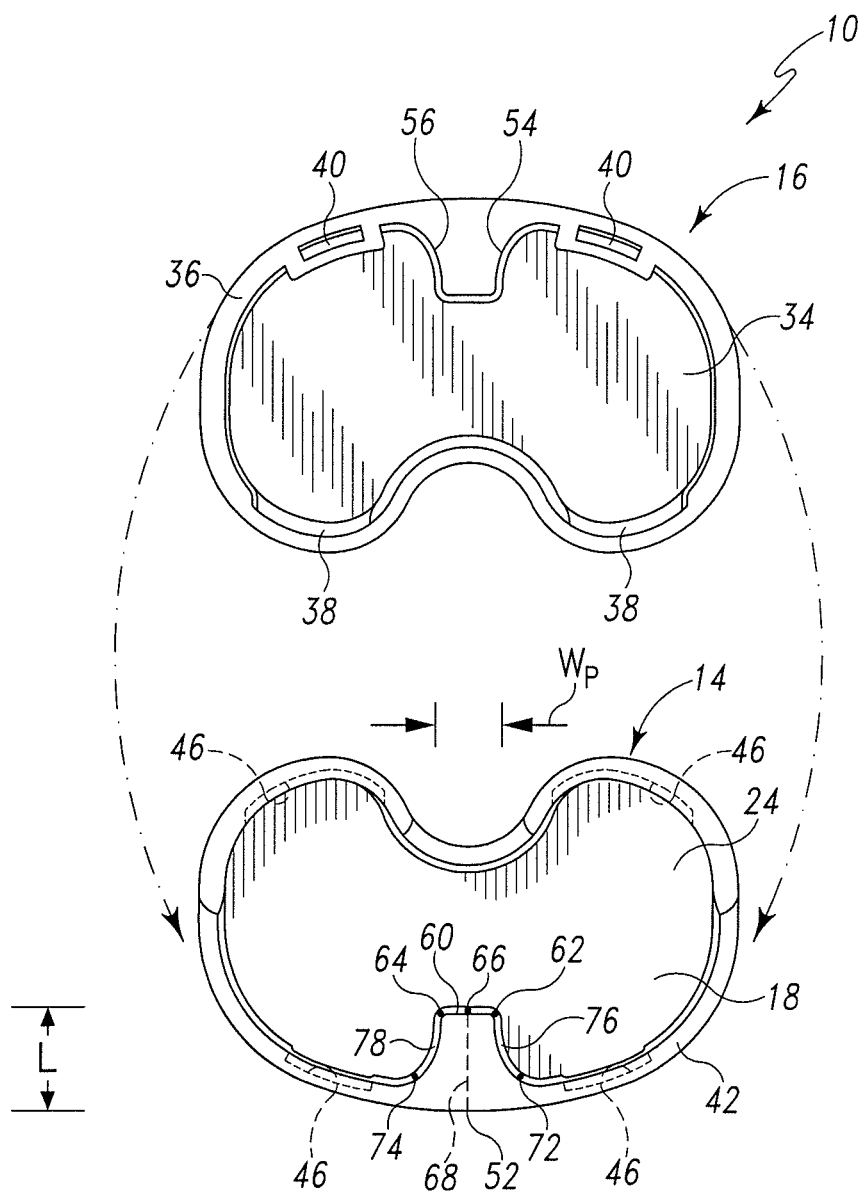
Figure 12:
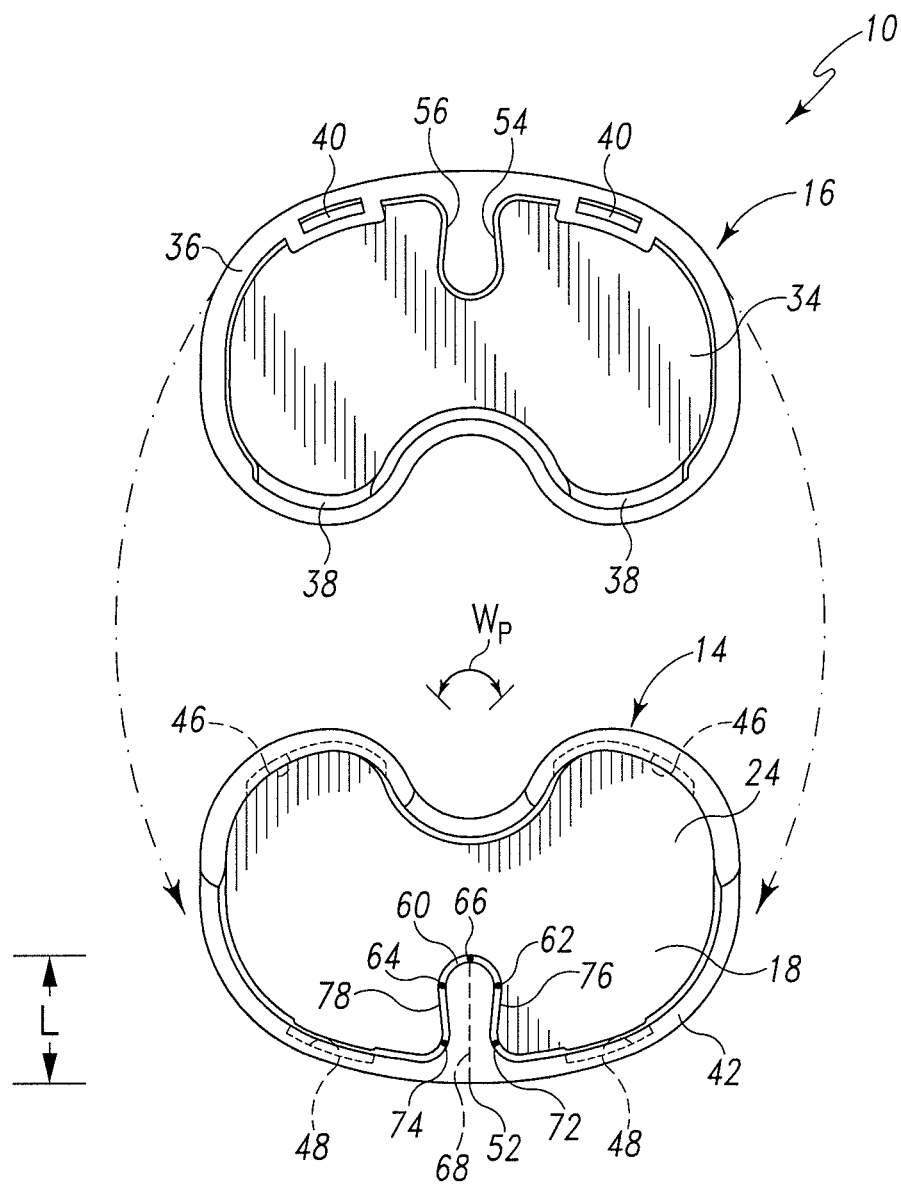

As shown in FIG. 11, other configurations or modifications of the retaining rail 50 are also contemplated. For example, the lateral-most edge 76 and the medial-most edge 78 of the retaining rail 50 may be embodied as arcuate lines which intersect the peripheral rail 42 (as opposed to straight lines). Further, as shown in FIG. 12, the posterior-most edge 60 of the retaining rail 50 may be rounded. In this case, the posterior width (Wp) of the retaining rail 50 (i.e., the distance between the lateral end 62 of the posterior-most edge 60 and the medial end 64 of the posterior most edge 60) is defined by the arc length of the arc segment. As with other embodiments described herein, the lateral-most edge 76 and the medial-most edge 78 of the retaining rail 50 extend linearly from the points 72, 74, respectively, on the peripheral rail 42 to the arcuate shaped posterior-most edge 60.

Figure 13:
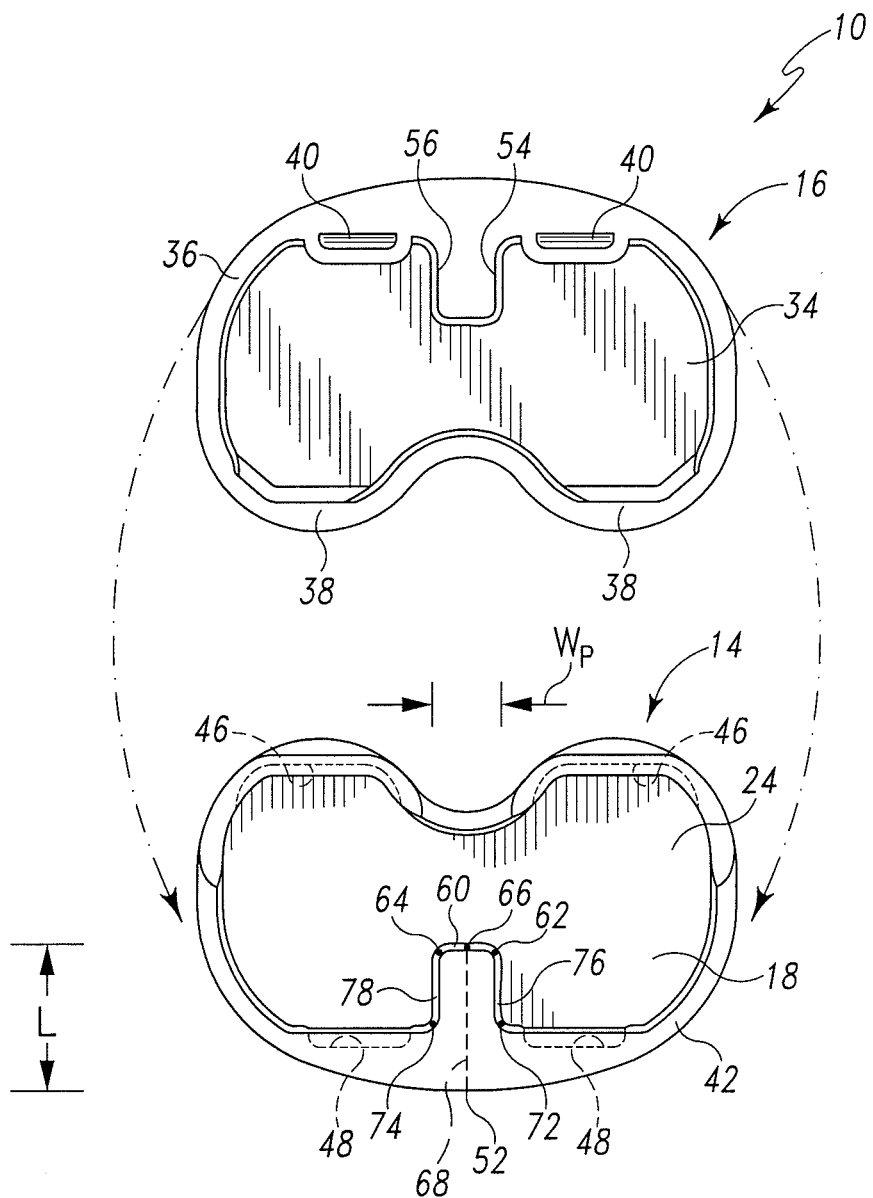

In addition to variations of the retaining rail 50, other modifications of the fixed-bearing knee prosthesis 10 are also contemplated. For example, as shown in FIG. 13, a portion of the peripheral rail 42 on the anterior side of the tibial tray 14 may be widened relative to the other designs described herein. Moreover, as also shown in FIG. 13, different designs of the posterior tabs 38 and the corresponding posterior undercuts 46 may also be used.

As described herein, the retaining rail 50 functions to restrict relative rotational motion between the bearing 16 and the tibial tray 14. The center of this rotation coincides approximately with the instantaneous center of torque exerted by the femoral component 12 on the bearing 16. Positioning the retaining rail 50 on the anterior portion of the peripheral rail 42 (as opposed to the posterior portion) effectively increases the distance from this center of rotation, thereby enhancing the ability of the retaining rail 50 to restrict rotation. The retaining rail 50 also functions to prevent substantial loading on the anterior holding elements (e.g., the anterior tabs 40).

The retaining rail 50 also functions as an alignment guide to facilitate assembly of the bearing 16 to the tibial tray 14. A user may assemble the bearing 16 to the tibial tray 14 entirely from the front (i.e., anterior to posterior), as described above. Alternatively, the user may load the bearing 16 from the front, but with the posterior lateral side engaged and the bearing 16 subsequently rotated into its locked position.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the apparatus, system, and method described herein. It will be noted that alternative embodiments of the apparatus, system, and method of the present disclosure may not include all of the features described yet still benefit from at least some of the advantages of such features. Those of ordinary skill in the art may readily devise their own implementations of the apparatus, system, and method that incorporate one or more of the features of the present invention and fall within the spirit and scope of the present disclosure as defined by the appended claims.

The invention claimed is:
1. A fixed-bearing knee prosthesis, comprising:
   a femoral component having a medial condyle surface and a lateral condyle surface,
   a bearing having (i) a medial bearing surface configured to articulate with the medial condyle surface of the femoral component, and (ii) a lateral bearing surface configured to articulate with the lateral condyle surface of the femoral component, and a tibial tray secured to the bearing, the tibial tray having a platform with an elongated stem extending downwardly from a lower surface thereof, the platform having (i) a peripheral rail extending along at least an anterior section of a perimeter of the platform and extending upwardly from an upper surface of the platform, and (ii) a retaining rail extending upwardly from the upper surface of the platform and posteriorly away from the peripheral rail, wherein (i) the retaining rail has a posterior width defined by the distance between a lateral end and a medial end of a posterior-most edge of the retaining rail, (ii) the retaining rail has a length defined by the distance of an imaginary center line segment extending from the anterior edge of the tibial tray to a midpoint located along the posterior-most edge halfway between the lateral end and the medial end, and (iii) the posterior width of the retaining rail is less than, or equal to, the length of the retaining rail.

2. The knee prosthesis of claim 1, wherein the peripheral rail extends along the entire perimeter of the platform.

3. The knee prosthesis of claim 1, wherein the peripheral rail has at least one undercut slot formed therein.

4. The knee prosthesis of claim 3, wherein the bearing has at least one tab positioned in the at least one undercut slot of the peripheral rail.

5. The knee prosthesis of claim 1, wherein:
the bearing has an upper surface and a lower surface,
both the medial bearing surface and the lateral bearing surface are defined in the upper surface of the bearing,
the lower surface of the bearing contacts the upper surface of the platform,
the lower surface of the platform has a recess formed therein, and
the retaining rail is positioned in the recess.

6. The knee prosthesis of claim 5, wherein:
the recess is bounded by a sidewall, and
the sidewall contacts the retaining rail.

7. The knee prosthesis of claim 1, wherein the retaining rail is contiguous with the peripheral rail.

8. An implantable orthopaedic component, comprising:
a tibial tray configured to be secured to a surgically prepared tibia of a patient, the tibial tray having a platform with an elongated stem extending downwardly from a lower surface thereof, the platform having (i) a peripheral rail extending along at least an anterior section of a perimeter of the platform and extending upwardly from an upper surface of the platform, and (ii) a retaining rail extending upwardly from the upper surface of the platform and posteriorly away from the peripheral rail, wherein (i) the retaining rail has a posterior width defined by the distance between a lateral end and a medial end of a posterior-most edge of the retaining rail, (ii) the retaining rail has a length defined by the distance of an imaginary center line segment extending from the anterior edge of the tibial tray to a midpoint located along the posterior-most edge halfway between the lateral end and the medial end, and (iii) the posterior width of the retaining rail is less than, or equal to, the length of the retaining rail.

9. The implantable orthopaedic component of claim 8, wherein the peripheral rail extends along the entire perimeter of the platform.

10. The implantable orthopaedic component of claim 8, wherein the peripheral rail has at least one undercut slot formed therein.

11. The implantable orthopaedic component of claim 8, wherein the retaining rail is contiguous with the peripheral rail.

12. A fixed-bearing knee prosthesis, comprising:
a femoral component having a medial condyle surface and a lateral condyle surface,
a bearing having (i) a medial bearing surface configured to articulate with the medial condyle surface of the femoral component, and (ii) a lateral bearing surface configured to articulate with the lateral condyle surface of the femoral component, and
a tibial tray secured to the bearing, the tibial tray having a platform with an elongated stem extending downwardly from a lower surface thereof, the platform having (i) a peripheral rail extending along at least an anterior section of a perimeter of the platform and extending upwardly from an upper surface of the platform, and (ii) a retaining rail extending upwardly from the upper surface of the platform and posteriorly away from the peripheral rail,
wherein the retaining rail has (i) a posterior-most edge having a lateral end and a medial end, (ii) a lateral-most edge extending linearly from a first point on the peripheral rail to the lateral end of the posterior-most edge, and (iii) a medial-most edge extending linearly from a second point on the peripheral rail to the medial end of the posterior-most edge.

13. The knee prosthesis of claim 12, wherein the peripheral rail extends along the entire perimeter of the platform.

14. The knee prosthesis of claim 12, wherein the peripheral rail has at least one undercut slot formed therein.

15. The knee prosthesis of claim 14, wherein the bearing has at least one tab positioned in the at least one undercut slot of the peripheral rail.

16. The knee prosthesis of claim 12, wherein:
the bearing has an upper surface and a lower surface,
both the medial bearing surface and the lateral bearing surface are defined in the upper surface of the bearing,
the lower surface of the bearing contacts the upper surface of the platform,
the lower surface of the platform has a recess formed therein, and
the retaining rail is positioned in the recess.

17. The knee prosthesis of claim 16, wherein:
the recess is bounded by a sidewall, and
the sidewall contacts the retaining rail.

18. The knee prosthesis of claim 12, wherein the retaining rail is contiguous with the peripheral rail.

* * * * *